(12) United States Patent
Schneiderman et al.

(10) Patent No.: US 6,687,621 B2
(45) Date of Patent: Feb. 3, 2004

(54) PREDICTIVE METHOD FOR POLYMERS

(75) Inventors: Eva Schneiderman, Fairfield, OH (US); David Thomas Stanton, Hamilton, OH (US); Toan Trinh, Maineville, OH (US); William David Laidig, Hamilton, OH (US); Michael Lee Kramer, Cincinnati, OH (US); Eugene Paul Gosselink, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 217 days.

(21) Appl. No.: 09/989,602

(22) Filed: Nov. 20, 2001

(65) Prior Publication Data

US 2002/0123848 A1 Sep. 5, 2002

Related U.S. Application Data

(60) Provisional application No. 60/252,342, filed on Nov. 20, 2000.

(51) Int. Cl.[7] .............................. G01D 1/02; G01D 1/04; G01D 1/16
(52) U.S. Cl. .............................. 702/27; 702/29; 702/30; 702/31; 702/32; 702/33; 703/2; 703/23; 703/27
(58) Field of Search ................................. 703/2, 23, 27; 702/27, 29, 30, 31, 32, 33

(56) References Cited

U.S. PATENT DOCUMENTS

| | | | | |
|---|---|---|---|---|
| 5,260,882 A | * | 11/1993 | Blanco et al. | 364/499 |
| 5,550,630 A | * | 8/1996 | Chrastil | 356/300 |
| 6,406,632 B1 | * | 6/2002 | Safir et al. | 210/656 |

FOREIGN PATENT DOCUMENTS

| WO | WO 02/44686 | * 6/2002 |
|---|---|---|

* cited by examiner

*Primary Examiner*—Gregory Delcotto
(74) *Attorney, Agent, or Firm*—Jason J. Camp; Kim W. Zerby; Steven W. Miller

(57) ABSTRACT

The present invention relates to a computational method for predicting a desired property and/or performance of polymers, and/or identifying and designing polymers that provide said desired property and/or performance, wherein the desired property can be provided by the neat, undiluted polymers, or diluted polymers in a composition. The method is a QSAR approach wherein the descriptors used are structural descriptors which are experimentally generated and/or derived from one or more analytical methods.

40 Claims, No Drawings

PREDICTIVE METHOD FOR POLYMERS

CROSS REFERENCE TO RELATED APPLICATIONS

This application claims priority under 35 U.S.C. § 119(e) to U.S. Provisional Application Serial No. 60/252,342, filed Nov. 20, 2000 (Attorney Docket No. 8342P).

TECHNICAL FIELD

The present invention relates to an improved computational method for predicting a property and/or performance of polymers, and/or identifying and designing polymers that provide said desired property and/or performance, wherein the desired property can be provided by the neat, undiluted polymers, or diluted polymers in a composition.

BACKGROUND OF THE INVENTION

An experienced chemist can tell much about the chemical reactivity or physical properties of a molecule just by looking at its structure. As the pool of chemical experience and knowledge accumulates, and the speed of computers increases, there is a growing desire to design methods to correlate the chemical and physical properties as well as other useful properties (such as biological activities) of the chemicals to their chemical structure.

The general method is described as a quantitative structure-activity relationship (QSAR) or quantitative structure-property relationship (QSPR), and is described in, e.g., H. Kubini in QSAR: Hansch Analysis and Related Approaches, published by VCH, Weinheim, Germany, 1993, and, D. J. Livingstone, Structure Property Correlations in Molecular Design, in Structure-Property Correlations in Drug Research, Han van de Waterbeemd, ed., Academic Press, 1996, said publications are incorporated herein by reference. In this method the structures of a representative set of materials are characterized using physical properties such as log P (base-10 logarithm of the octanol-water partition coefficient P), fragment constants like Hammett's sigma, or any of a large number of computed molecular descriptors (for example, see P. C. Jurs, S. L. Dixon, and L. M. Egolf, Representations of Molecules, in Chemometric Methods in Molecular Design, Han van de Waterbeemd, ed., published by VCH, Weinheim, Germany, 1995.

In the general case, a "representative set", sometimes also called a "training set", of materials is a collection of materials that represent the expected range of change in both the property of interest (the property to be predicted using the model) and also the range of molecular structure types to which the model is designed to apply. The size of the set of materials necessary to constitute a "representative set" is dependent on the diversity of the target structures and the range of property values for which the model needs to be valid. Typically, one needs to have about 20 to about 25 materials to begin to generate statistically valid models. However, it is possible to obtain valid models with smaller sets of materials if there is a large degree of similarity between the molecular structures. A general rule of thumb suggests that the final model should include at least about five unique materials in a training set for each parameter (molecular descriptor or physical property) in the model in order to achieve a statistically stable equation and to avoid "overfitting", the inclusion of statistical noise in the model. The range of the experimental property being modeled must also be broad enough to be able to detect statistically significant differences between members of the representative set given the magnitude of the uncertainty associated with the experimental measurement. For biological properties, a typical minimum range is about two orders of magnitude (100 fold difference between the lowest and highest values) because of the relatively large uncertainty associated with biological experiments. The minimum range requirement for physical properties (e.g. boiling points, surface tension, aqueous solubility) is usually smaller because of the greater accuracy and precision achieved in measuring such properties.

There are practical limits to the size of the molecules that can be studied using known QSAR techniques. Typically, these methods are applied to small organic molecules. The term "small" usually refers to non-polymeric materials with less than about 200 atoms including hydrogens. The practical reason for this limitation is that the vast majority of calculated molecular descriptors begin to lose the ability to distinguish one structure from another as the size of the molecules gets larger. For example, the addition of one methyl group (a carbon and three hydrogens) to benzene increases the molecular weight (an example of a molecular descriptor) by about 17.9% whereas the addition of the same methyl group to a $C_{100}$ linear alkane changes the molecular weight by less than 1%.

The model developed is often a multivariate, (involving many parameters, linear regression equation that is computed by regressing a selected set of molecular descriptors or physical properties against measured values of the property of interest (e.g., $Y=m_0+m_1x_1 \ldots +m_nx_n$, wherein Y is the measured property of interest, $x_1, x_2 \ldots x_n$ are the molecular descriptors or physical properties, $m_0, m_1 \ldots m_n$ are the regression coefficients, and n is the number of descriptors or physical properties in the model). A number of different methods have been employed for the selection of the parameters to be included in the regression equation, such as stepwise regression, stepwise regression with progressive deletion, best-subsets regression, etc. More recently, evolutionary methods such as genetic algorithms, or learning machines such as neural networks have been used for parameter selection.

The first indicator used to judge the quality of a regression model is the coefficient of multiple determination, or $R^2$. This measures the proportion of the variation of the observed property (the property being modeled, the dependent variable) that is accounted for by the set of descriptors (independent variables) in the model. The correlation coefficient between the fitted property values (calculated using the model) and the experimentally observed property values is termed the coefficient of multiple correlation, commonly called the correlation coefficient, or R, which is the positive square root of $R^2$. All commercial statistical packages report $R^2$ as a standard part of the results of a regression analysis. A high $R^2$ value is a necessary, but not a sufficient condition for a good model. It's important that a model account for as much variation in the dependent variable as possible. However, the validity of the model must be determined using a variety of other criteria.

Once a model has been developed, it must be validated. This process includes the consideration of statistical validation of the model as a whole (e.g., overall-F value from analysis of variance, AOV) and of the individual coefficients of the equation (e.g., partial-F values), analysis of collinearity between the independent variables (e.g. variance inflation factors, or VIF), and the statistical analysis of stability (e.g., cross-validation). Most commercial statistics software can compute and report these diagnostic values. If possible, one employs an "external prediction set", a set of materials for which the property of interest has been measured, but which were not included in the development of the model, to evaluate and demonstrate the predictive accuracy of the model.

A wide variety of software is available to perform various parts of the model development process. Descriptors can be pulled from databases (e.g., in the case of fragmental constants), or computed directly from the molecular structure of the materials. Non-limiting examples of programs which can be used to compute descriptors are SYBYL (Tripos, Inc., St. Louis, Mo.), Cerius2 (Accelrys, Princeton, N.J.), and ADAPT (P. C. Jurs, Pennsylvania State University, University Park, PA). These same programs can also be used to perform the statistical model development which includes the determination of the correlation coefficient between the computed estimates and the experimentally-derived property of interest plus subsequent model validation. Alternatively, commercial statistical programs like Minitab for Windows (Minitab, INC., State College, Pa.) can be used to generate and validate model equations.

One approach for describing the chemical structure of the chemical molecules in detail that is commonly used in QSAR/QSPR work is the group contribution method. In this approach, the structure of the molecule is divided into small fragments. The software keeps track of the number and type of each fragment. A database is then searched and a fragment-constant is found for each fragment in the structure. The physical property is then estimated by calculating the sum of constants for all fragments found in the structure multiplied by the number of times that fragment is found in the structure. For example, the group contribution method is used to compute and predict log P, the base-10 logarithm of the partition coefficient P, as described in A. Leo, Comprehensive Medicinal Chemistry, Vol. 4, C. Hansch, P. G. Sammens, J. B. Taylor and C. A. Ramsden, Eds., p. 295, Pergamon Press, 1990, incorporated herein by reference. Alternatively, a model developed to estimate and predict normal boiling points using whole-molecule structure descriptors is described in "Development of a Quantitative Structure—Property Relationship Model for Estimating Normal Boiling Points of Small Multifunctional Organic Molecules", David T. Stanton, Journal of Chemical Information and Computer Sciences, Vol. 40, No. 1, 2000, pp. 81–90, incorporated herein by reference. In this approach, the structure is not divided into fragments. Rather, measurements of a variety of structural features are computed using the whole structure. For most of these small molecules, the chemical structure can be described quickly and accurately using these types of approaches.

There are also efforts to apply QSAR/QSPR methods to various classes of polymers including homopolymers and copolymers. A polymer is a chemical compound or mixture of compounds formed by polymerization and consisting essentially of repeating structural units called monomers. A homopolymer is comprised of essentially one type of monomer. A copolymer is comprised of more than one type of monomer. Approaches that are useful for small molecules however, are typically not applicable for developing predictive polymer QSAR's. The number of atoms in the polymer molecule is usually much larger, and thus to develop the necessary descriptors for the group contribution method requires very large sets of experimental data. If a polymer contains a structural unit whose additive contribution to a certain property can not be estimated, the value of that property can not be predicted for that polymer. Attempts to by-pass the need for large sets of experimental data necessary to develop group contribution descriptors can result in time consuming force-field or quantum mechanical calculations, which often fail to provide accurate descriptors. Both approaches have been investigated by A. J. Hopfinger, M. G. Koehler, R. A. Pearlstein, and S. K. Tripathy in Journal of Polymer Science, Polymer Physics Edition, Vol. 26, 1988, pp. 2007–2028, and by J. Bicerano in Prediction of Polymer Properties, $2^{nd}$ edition, Marcel Dekker, Inc., New York, Basel, 1996, incorporated herein by reference. Furthermore, except for some natural polymers such as enzymes, most polymers, especially synthetic polymers are mixtures of polymeric molecules of various molecular weights, sizes, structures and compositions. Commercially available polymers, especially those that are used by industry in large scale, commonly contain certain levels of unreacted fragments and/or by-products. In most cases, there is not one exact chemical formula or structure that can describe such a polymer. Such polymers are characterized most commonly by their average properties, such as, average molecular weight, viscosity, glass transition temperature, melting point, solubility, cloud point, heat capacity, interfacial tension and adhesion, refractive index, stress relaxation, sheer, conductivity, permeability, and the like. Another common way that polymers are characterized is by the number and type of monomers. Polymers are also sometimes defined by the amounts of starting ingredients used in the polymerization process; from the starting ingredients and the conditions under which the polymerization reaction proceeds, one can sometimes derive a generalized structure and/or formula of the resulting polymer.

Applications of QSAR/QSPR approaches to polymers typically use descriptors derived for repeated units, such as molecular weight of a repeat unit, end-to-end distance of a repeat unit in its fully extended conformation, Van der Walls volume of a repeat unit, positive and negative partial surface area normalized by the number of atoms, topological Randic index computed for a repeating unit, cohesive energy which can be estimated using group contribution method, and a parameter related to the number of rotational degrees of freedom of the backbone of a polymer chain, that can be derived from the structure of a repeat unit, as described by J. T. Seitz in Journal of Applied Polymer Science, Vol. 49, 1993, pp. 1331–1351, or by topological connectivity indices as described by J. Bicerano in Prediction of Polymer Properties, $2^{nd}$ edition, Marcel Dekker, Inc., New York, Basel, 1996, both of which are incorporated herein by reference.

Most QSAR/QSPR polymer models correlate theoretically calculated molecular descriptors of a repeating unit with bulk physical properties of the polymer, such as glass transition temperature, refractive index, heat capacity, diamagnetic susceptibility, viscosity, thermal conductivity, and the like. In addition, development of these models requires atomic and/or group correction terms. Another approach to predicting properties of homopolymers of a regular structure is to model three repeating units for each polymer and calculate descriptors only for the middle unit. In this way influence of the adjacent units can be also taken into account, as described by Katritzky A. R. et al. in Journal of Chemical Information and Computer Sciences vol. 38, 1998, pp 300–304, incorporated herein by reference. However, a limitation of these models is that they are applicable only to homopolymers and can not be easily reapplied to block and/or random copolymers.

One approach to predicting properties of copolymers is via development and calculation of applicable group contribution descriptors and to extend existing group contribution tables. This, however, requires large experimental data sets. An approach to overcome this deficiency for alternating block copolymers is to treat blocks of a copolymer as separate polymers and assume simple additivity rules for prediction of extensive properties as described by J. Bicerano in Prediction of Polymer Properties, $2^{nd}$ edition, Marcel Dekker, Inc., New York, Basel, 1996, incorporated herein by reference. Calculation of the properties of random copolymers require using weighted averages (from molar fractions of repeating units) of all extensive properties and appropriate definitions for the intensive properties in terms of the extensive properties as described by J. Bicerano in Prediction of Polymer Properties, $2^{nd}$ edition, cited herein above.

The present invention relates to a novel approach of QSAR for polymers wherein the descriptors used are structural descriptors, which are experimentally generated and/or derived using one or more analytical methods. The term polymer as used herein comprises both homopolymer and copolymer, and mixtures thereof.

SUMMARY OF THE INVENTION

The present invention relates to a method for identifying a predictive model from which to select existing polymers, and/or to prepare new polymers having a desired property, the method comprising the steps of:

a. identifying a set of existing polymers including representatives having a broad range of values of the desired property;

b. determining the desired property for each of the polymers in the set, wherein the property of each polymer has a numerical value;

c. generating quantitative structural descriptors that characterize at least a portion of the molecular structure, preferably characterizing the whole molecular structure, of each polymer of the set of polymers; and d. identifying a mathematical function that relates a selected group of quantitative structural descriptors to the desired property, said group comprises at least 2, preferably at least 3 quantitative structural descriptors, preferably from 2 to about 10, more preferably from 2 to about 6, and even more preferably from 2 to 4 quantitative structural descriptors, the predictive model comprising the identified mathematical function;

wherein the desired property can be provided by the neat, undiluted polymer, but preferably the desired property is provided by the polymer in a composition, more preferably the desired property is a useful functional property in a consumer product composition and/or industrial composition, and even more preferably the desired property is a consumer relevant property provided by the polymer under use conditions in a consumer product composition comprising the polymer.

The method of the present invention can further comprise the steps of e. identifying one or more additional mathematical function(s); and f. determining which mathematical function more accurately correlates molecular structure with the desired property.

DETAILED DESCRIPTION OF THE INVENTION

The present invention relates to a method for identifying a predictive model from which to select existing polymers, and/or to prepare new polymers having a desired property, the method comprising the steps of:

a. identifying a set of existing polymers including representatives having a broad range of values of the desired property, the set typically comprising at least about 10 unique polymer samples, preferably at least about 15 unique polymer samples, more preferably at least about 20 unique polymer samples, and even more preferably at least about 25 unique polymer samples;

b. determining the desired property for each of the polymers in the set, wherein the property of each polymer has a numerical value;

c. generating quantitative structural descriptors that characterize at least a portion of the molecular structure, preferably characterizing the whole molecular structure, of each polymer of the set of polymers, said structural descriptors are experimentally determined or derived using one or more analytical methods; and d. identifying a mathematical function that relates a selected group of quantitative structural descriptors, and additionally comprising optional descriptors selected from the group consisting of computed structural descriptors for the whole molecule, monomers and/or subunits; bulk physical property descriptors; compositional descriptors; and mixtures thereof; to the desired property, said group comprises at least 2, preferably at least 3 descriptors, preferably from 2 to about 10, more preferably from 2 to about 6, and even more preferably from 2 to 4 descriptors, wherein the descriptors are preferably distinct descriptors, the predictive model comprising the identified mathematical function; the preferable model is the one that is statistically valid and yields the best fit with the smallest number of descriptors;

wherein the desired property can be provided by the neat, undiluted polymer, but preferably the desired property is provided by the polymer in a composition, more preferably the desired property is a useful functional property in a consumer product composition and/or industrial composition, and even more preferably the desired property is a consumer relevant property provided by the polymer under use conditions in a consumer product composition comprising the polymer.

The method of the present invention can further comprise the steps of e. identifying one or more additional mathematical function(s); and f. determining which mathematical function more accurately correlates molecular structure with the desired property.

The term "predictive model" as defined herein means a mathematical function that uses the quantitative structural descriptors generated in step "c" above to calculate predicted values of the property of interest which can be correlated with the experimentally derived values with a correlation coefficient of at least about 0.6, preferably at least about 0.7, more preferably at least about 0.8, and even more preferably at least about 0.9.

By "broad range of values of the desired property", it is meant that the set of selected existing polymer samples includes both samples with a high value for the desired property and those with no (numerical value of 0) or a low value for the desired property, and those with values distributed between the two extremes. The property values must be quantitative measures if one is to develop a predictive regression equation. If one is developing a classification model (e.g., active vs. inactive, or soft vs. not-soft) then this quantitative restriction does not apply.

The term "existing polymer" as used herein means that the polymer is physically available, either commercially or experimentally synthesized, to be studied and/or to be formulated in compositions to be studied. The term "new polymer" means that the polymer is currently not known and/or not available broadly, or does not currently exist.

By "quantitative structural descriptor" it is meant a structural chemical property that has a numerical value to characterize at least a portion of the molecular structure, preferably characterizing the entire molecular structure of the polymer, such as molecular weight, molecular weight distribution, structure type, weight and/or molar percentage (s) of one or all atomic elements, average weight and/or molar percentage of each molecular group, number of each molecular group, number of each monomer, degree of unsaturation, degree of branching (number of side groups or number of branching groups) within a molecule and/or part of a molecule, weight percentage of each atomic element in a branching group, number of each molecular group in a branching group, number of each type and/or number of functional groups and/or their percentage, types and/or number and/or percentage of repeating units, monomer units or other subunits, the spread of the distribution of a value above (as characterized by, e.g., variance, deviation, range, and the like), and mixtures thereof; and functional transforms thereof (e.g., square root ($\sqrt{x}$), base-10 logarithm (log x), inverse (1/x), and the like); and mixtures thereof. Each structural chemical property is an average property of the polymer and is experimentally determined or derived using one or more analytical methods such as, but not limited to, nuclear magnetic resonance, infrared spectroscopy, UV/visible spectroscopy, fluorescence spectroscopy, quantitative hydrolysis, elemental analysis, chromatography, mass spectrometry, light scattering, osmometry, electrophoretic techniques, quantitative gravimetric analysis, and the like.

By "computed structural descriptor" it is meant a structural property of the whole molecule, monomers and/or subunits that are generated by a computer program or by measuring physical molecular models, such as, but not limited to, length, width, depth, cross section area, volume, and surface area, topological indices for the monomer units or other subunits, electronic descriptors for the monomer units or other subunits, such as, but not limited to, electric and magnetic moments, polarizabilities, orbital energies and excitation energies, solubility descriptors such as the octanol/water partition coefficient and aqueous solubility, charged partial surface area (CPSA) descriptors, and the like.

By "bulk physical property descriptor" it is meant a property that describes a physical state or behavior of the polymer in an aggregated condition wherein a very large number of molecules exist together, such as, but not limited to, viscosity, glass transition temperature, melting point, density, solubility, cloud point, heat capacity, interfacial tension, interfacial adhesion, refractive index, stress relaxation, sheer, conductivity, permeability, diamagnetic susceptibility, thermal conductivity, and the like.

By "compositional descriptor" it is meant the content of the starting ingredients used in the preparation of the polymers, e.g., weight percent of one or more starting ingredients, including catalyst(s), and/or reaction conditions, e.g., reaction temperature(s), reaction time(s), reaction pressure, and the like.

For simple models wherein the polymers have rather similar general structures and/or compositions, the model for the desired property can be formed with using a small number of descriptors, typically from 2 to about 10, preferably from 2 to about 6, and more preferably from 2 to about 4. However, the number of descriptors needed for a good model is a function of the number of structures in the training set and their diversity. For some data sets, with polymers having broadly diverse structure, even more than 10 descriptors may be needed to generate a satisfactory model. Therefore, in general, the preferred model is the one that is statistically valid and yields the best fit with the smallest number of descriptors. By "best fit" it is meant that the model yields the largest $R^2$ value. However, in another aspect of the present invention, the steps e and f described herein above allow a development of several models which have more or less similar $R^2$ values, but relate to different sets of descriptors. For practical purpose, it can be desirable to select as the best model the one that relates to a set of descriptors that are easiest to describe the polymers experimentally and/or structurally, e.g., for molecular design purpose, and/or to explain the desired property, even though that preferred model may not have the largest $R^2$.

The term "distinct" in "distinct descriptor" as used herein means that the model comprises "orthogonal" or "non-correlated" descriptors. Two descriptors are defined as orthogonal if the inner product of their vectors is equal to zero. Because of their nature, these quantitative structural descriptors are rarely perfectly orthogonal. The degree to which the model may be affected by deviations from orthogonality or non-correlation (also known as collinearity) is determined at validation time by examining the model for potential problems relating to collinearity using a statistical test called variance inflation factors (VIF). It is preferable that the individual VIFs for each descriptor be less than about 10, and the average VIF for the model be about 1. However, it should be noted that descriptors in validated and useful models can yield VIF values greater than 10. It is preferred that the sets of values for the descriptors used in the model are less than 90%, preferably less than 80% and more preferably less than 70% collinear.

The term "functional transform" means defining a new descriptor f(x) of a descriptor x where f( ) is any single variable mathematical function such as powers and inverse powers (e.g., $1/x$, $\sqrt{x}$, $x^2$, $x^{-3.2}$), logarithms ($\log_{10}x$, $\log_e x$), trigonometric (e.g., sin x), inverse trigonometric (e.g., $\cos^{-1}x$), hyperbolic (e.g., tan hx), inverse hyperbolic (e.g., sin $h^{-1}x$), and the like.

The polymer herein can have different structures and/or compositions. They can be homopolymer or copolymer, linear, branched, graft, star, ladder, dendritic, cyclic, crosslinked, and the like, the copolymer can be random or block. Depending on the size, type and/or structure, the average molecular weight of the polymer can be determined by one or more analytical methods. Nonlimiting examples of such analytical methods for molecular weight determination include gel permeation chromatography, size-exclusion chromatography, reverse and normal phase, liquid chromatography, capillary electrophoresis and other electrophoretic techniques, with conventional universal calibration with various detection techniques, including but not limited to triple detection, refractive index, multiple-angle laser light scattering, viscometry, evaporative light scattering, UV-VIS, fluorescence, and the like. Other methods include sedimentation, viscometry (neat viscosity or solution viscosity), osmometry, light scattering, mass spectrometry (including, e.g., MALDI (matrix assisted laser desorption ionization), ESI (electrospray ionization), APCI (atmospheric pressure chemical ionization), desorption, FAB (fast atom bombardment)), and the like. Molecular weight can also be determined by a combination of analytical methods, such as a combination of $^{29}$Si-NMR and $^{13}$C-NMR, and a hydroiodic acid sample hydrolysis followed by a quantitative GC analysis of the resulting alkyliodides, for use to structurally characterize polyalkyleneoxy polysiloxanes of the graft type and the ABA type.

It is preferred that the desired property provided by the polymers identified or predicted by the method of the present invention is a consumer relevant property under use conditions in a consumer product composition comprising the polymer or a useful functional property in an industrial composition. Such a consumer relevant property can be determined instrumentally by one or more apparatus, or by the senses, such as fabric softness or fabric feel. Sensory, or sensorial properties can be quantitatively determined by many methods, e.g., methods given in "Manual on Sensory Testing Methods", published as ASTM Special Technical Publication 434 by the American Society for Testing and Materials, Philadelphia, Pa., said publication is incorporated herein by reference.

Nonlimiting examples of consumer composition include fiber and fabric care composition, hair care composition, skin care composition, cosmetic composition, nail care composition, lip care composition, oral and/or dental care composition, pet care composition, hard surface care composition, soft surface care composition, home care composition, car care composition, food composition, beverage composition, disposable paper composition, baby care composition, human health care composition, animal health care composition, and the like. Nonlimiting examples of a desired functional property of a fiber and fabric care composition include fabric color restoration, color maintenance, fading reduction, fabric softening, fabric conditioning, wrinkle control, wrinkle resistance or reduction, shape retention, wear resistance or reduction, pilling prevention and/or reduction, soil release, static control, shrinkage reduction, long lasting freshness, odor control, flame resistance, waterproofing, allergen control, and the like. Nonlimiting examples of a desired functional property of a car care composition include long lasting shine/gloss, color deepening and/or maintenance, glide/lubricity, and the like. Nonlimiting examples of a desired functional property of a hair care composition include long lasting shine, ease of combing and the like.

Nonlimiting examples of industrial composition include textile treatment compositions, coating compositions, ink, including printing ink, compositions, wood treatment compositions, adhesive compositions, fluid drilling compositions, wax compositions, plastic molding compositions, and the like.

The method of the present invention can be applied to different classes of polymers. The polymer training set can be very diverse comprising polymers with very different structures. However, the process is more simple when the set of polymers belong to a class having rather similar general structures. Nonlimiting examples of such classes of polymers include polysiloxanes and derivatives thereof; polyethyleneoxy/polypropyleneoxy block copolymers, derivatives thereof, homologues thereof, and mixtures thereof; polysaccharide polymers, homologues thereof, derivatives thereof (e.g., alkyl, acyl, carboxy-, carboxymethyl-, nitro-, sulpho-, and mixtures thereof), and mixtures thereof; polyvinyl homopolymers and/or copolymers, and derivatives thereof, such as, polyvinyl acetate and partially hydrolyzed materials thereof, polyvinyl alcohol, block and/or random copolymers of polyvinyl pyridine N-oxide, polyvinyl pyrrolidone, polyvinyl imidazole, block and/or random copolymer of polyvinyl pyrrolidone and polyvinyl imidazole, including structural homologs and derivatives thereof, e.g., including charged, hydrophilic, and/or hydrophobic modifying groups, e.g., ethoxylated, propoxylated, alkylated, and/or sulfonated groups, polystyrene, block and/or random copolymer of polystyrene with polymaleate, polyacrylate, or polymethacrylate, polyvinyl carboxylic acids (e.g., polyacrylic acid, polymethacrylic acid), alkyl esters thereof, amides thereof, and mixtures thereof, polyamines and chemically modified derivatives thereof, e.g., alkylated, ethoxylated, polyethoxylated, propoxylated, polypropoxylated, acylated, and the like, and mixtures thereof, polyamide, homologues thereof and/or derivatives thereof (e.g, proteins, peptides, nylon), and polyamideamines, and mixtures thereof; polyterephthalates, isomers thereof, homologues thereof, and/or derivatives thereof, e.g., sulfated. sulfonated,. ethoxylated, alkylated (e.g., methyl, ethyl, and/or glycerol) derivatives, and mixtures thereof; polyesters and chemically modified derivatives thereof; polyurethane; condensation products of imidazole and epichlorhydrin, including charged, hydrophilic, and hydrophobic modifying groups, e.g., ethoxylated, propoxylated, alkylated, and/or sulfonated groups, and mixtures thereof; aromatic polymeric condensates of formaldehyde, including ether-bridged and methylene-bridged phenols, naphthalenes, substituted naphthalenes; and mixtures thereof. The copolymers given herein above can be further modified to provide desired properties by incorporation of one or more of aryl, alkyl, allyl, methyl, ethyl, ethoxylate, propoxylate, nitro, amino, imido, sulpho, carbo, phospho, groups, and the like. The polymers can have any architecture, including block, random, graft, dendritic, and the like.

Following is a nonlimiting illustrative example of the method of the present invention. This example relates to polyalkyleneoxy polysiloxane polymers for use in an aqueous fabric softening spray composition and in an article of manufacture comprising such fabric softening composition. Polyalkyleneoxy polysiloxane polymers are also known by other names, including polyalkyleneoxy polysiloxanes, silicone copolyols, silicone glycol copolymers, silicone glycol surfactants, silicone polyoxyalkylene copolymers, silicone poly(oxyalkylene) copolymers, siloxane polyethers, polyalkylene oxide polysiloxanes, polyalkylene oxide silicone copolymers, and dimethicone copolyols. Polyalkyleneoxy polysiloxane polymers that are used to develop the predictive fabric softness model of the present invention comprise a polysiloxane polymer backbone and one or more polyalkyleneoxy side chains, and having the general formula:

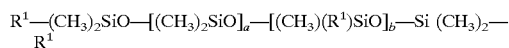

wherein each $R^1$ is the same or different and is selected from the group consisting of methyl; polyethyleneoxy/polypropyleneoxy group; optionally allyl group; and mixtures thereof; with at least one $R^1$ being a polyethyleneoxy/polypropyleneoxy group, wherein the polyethyleneoxy/polypropyleneoxy group has the general formula:

wherein n is 3 or 4, preferably 3, and each $R^2$ is the same or different and is selected from the group consisting of hydrogen, $C_1$–$C_4$ alkyl group, acetyl group, and the like;

said polyalkyleneoxy polysiloxane is selected from the group consisting of polyethyleneoxy polysiloxanes (c is not 0 and d=0), polyethyleneoxy/polypropyleneoxy polysiloxanes (both c and d are not 0), and mixtures thereof; and said polyalkyleneoxy polysiloxane has a molecular weight of at least about 600, preferably at least about 1000.

The most common molecular structures for polyalkyleneoxy polysiloxane polymers include the graft copolymers (also called the rake-type or comb copolymers, or the alkyl-pendant copolymers) and the ABA copolymers. The graft copolymers have the general structure:

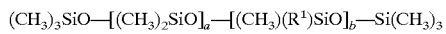

$(CH_3)_3SiO-[(CH_3)_2SiO]_a-[(CH_3)(R^1)SiO]_b-Si(CH_3)_3$ wherein the polyalkyleneoxy groups ($R^1$) are attached along a linear polysiloxane backbone through a series of hydrolytically stable Si—C bonds. A special type of graft copolymers are the "trisiloxanes" wherein a=0 and b=1.

The ABA copolymers are linear and have the general structure:

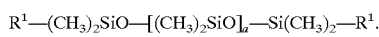

$R^1-(CH_3)_2SiO-[(CH_3)_2SiO]_a-Si(CH_3)_2-R^1$.

It is found that some commercially available polyalkyleneoxy polysiloxane polymers, including both polyethyleneoxy polysiloxanes and polyethyleneoxy/polypropyleneoxy polysiloxanes, can be formulated into aqueous spray compositions to be applied on fabrics from a sprayer to provide various levels of fabric softening performance, as judged by sensory evaluation, namely, tactile feel.

The general method that is used herein for determining the softness performance of an aqueous composition comprising each polyethyleneoxy polysiloxane is a pair comparison of fabrics sprayed with said composition and fabrics sprayed with water. The grading scale is a "panel score unit" (PSU) scale, in which expert graders compare the fabrics treated by the two different treatments for fabric softness feel, and assign a grade according to the following grade scale: PSU=1 means "I think there is a difference", PSU=2 means "I know there is a difference", PSU=3 means "I know there is a large difference", and PSU=4 means I know there is a very large difference.

For a better scaling, to be able to compare and quantitatively rank the performance of all of the polymers, the performance of the composition comprising each polymer is compared with both water (used as a low benchmark) and with a composition comprising a polymer which is found to provide a good softness performance (used as a high benchmark). All possible pairs of the three treatments are compared for softness in a round robin fashion, using the PSU method, and the softness scores are derived using an analysis of variance method which is based on the Scheffe method, as described in "An analysis of variance for paired comparison", H. Scheffe, Journal of American Statistical Association, Vol. 47, pp. 381–400 (1952), incorporated herein by reference. When there are many polymers to be compared, such as in the present case, it is preferred for each test to comprise two test compositions each comprising a different polymer to be evaluated, a low bench mark (water) and a common high benchmark composition, and having all possible pairs of the 4 treatments compared for softness in a round robin fashion. Then the softness scores for all treatments are rescaled, with the softness score for water set at 0, and the score for the high benchmark treatment set at the same value across all tests for all polymers (the softness score for each polymer is an average score from at least three independent evaluations), so that softness scores for all polymers are on the same scale, and thus the performance of all polymers can be quantitatively compared.

To generate the predictive mathematical function for the fabric softening performance of polyethyleneoxy polysiloxanes in the spray composition context, the quantitative softness performance for a polymer is determined by (1) uniformly spraying test cotton terry cloths with an aqueous composition comprising about 1% of the polymer, by weight of the composition, at a level of about 40% of composition by weight of the fabric, (2) letting the fabrics dry, and (3) evaluating the performance by the method given herein above. The resulting softness scores for all polymers are then multiplied by 10, to get the softness performance index S for each polymer. The softness performance index S is thus expressed in numerical values, ranging from high values (e.g., S=20–28) representing high performance, to low values (e.g., S=0–9) as compared to water which has a softness performance index of 0.

The existing polymers for use in the development of this predictive model are some polyalkyleneoxy polysiloxane polymers that are commercially available from CK Witco Corp., Greenwich, Conn. under the trade name Silwet® surfactants, and from Dow Coming Corporation, Midland, Mich. as, e.g., DC silicone copolyols. The resulting predictive model can be used to select existing polyalkyleneoxy polysiloxane polymers that can provide a good fabric softening performance benefit from an aqueous spray composition, and/or to prepare new polyalkyleneoxy polysiloxane polymers that provide a good fabric softening performance from an aqueous spray composition.

A group of 38 existing, commercially available polyalkyleneoxy polysiloxane polymers including both polyethyleneoxy polysiloxanes and polyethyleneoxy/polypropyleneoxy polysiloxanes, which provide different levels of fabric softness ranging from high performance to practically no performance as compared to a control composition comprising water without any polyalkyleneoxy polysiloxane polymer, are selected as a "representative set" to develop the predictive softness model S.

The polyalkyleneoxy polysiloxane polymers of the representative set are characterized structurally by analytical methods to generate quantitative structural descriptors as described hereinbelow. The structural parameters generated to be used as structural descriptors for the development of the predictive model herein include, but are not limited to, t#Si (average total number of silicon atoms per one polymer molecule), t#triSi (average number of trimethyl siloxane, i,e., $Me_3SiO-$, units per polymer molecule), #branch (average number of branching points, i.e., average number of pendant groups per polymer molecule), #allyl (average number of unreacted allyl groups, i.e., average number of failed pendant units per polymer molecule), t#EO (average total number of ethyleneoxy units per polymer molecule), t#PO (average total number of dimethyl silicones per polymer molecule), t#diSi (average total number of dimethyl silicone , i.e., $-Me_2SiO-$, units per polymer molecule, %EO (average weight percent of all EO units), %PO (average weight percent of all PO units), %Si (average weight percent of silicone groups per polymer molecule), %Si atom (average weight percent of all silicon atoms in the polymer molecule), #EO/branch (average number of ethyleneoxy units in one branching unit), #PO/branch (average number of propyleneoxy units in one branching unit), MW (average molecular weight), $w_{Si}$ (mass ratio of all siloxane units), $w_{EO}$ (mass ratio of all ethyleneoxy units), $w_{PO}$ (mass ratio of all propyleneoxy units). Additional descriptors and analytical methods that are used to determined these structural descriptors are given hereinbelow. Several functional transforms of each structural parameter x, such as log x, √x, 1/x, and the like, are also used as structural descriptors for the development of the predictive model.

The multivariate statistical analysis ADAPT program (Automated Data Analysis and Pattern recognition Toolkit), available from P. C. Jurs, Pennsylvania State University, University Park, PA is used to develop the predictive model. After several mathematical predictive functions are built and evaluated, the final group of 3 quantitative structural descriptors comprising √(t#diSi), √(%Si) and √(t#EO) are used to develop the predictive softness model S as the following mathematical function (I):

$$S=3.246(\sqrt{t\#diSi})-1.880(\sqrt{\%Si})-0.9066\sqrt{t\#EO}+17.70 \quad (I)$$

wherein S is the Softness Index; t#diSi is the average total number of the $Si(CH_3)_2O$ units in the molecule; %Si is the weight percent of total silicone (or siloxane) in the molecule; and t#EO is the average total number of the ethyleneoxy $CH_2CH_2O$ units in the molecule.

This mathematical predictive function (I) generates predicted softness index values for the structural descriptors, which can be correlated with the experimentally derived values with a correlation coefficient of about 0.90. This excellent fit is particularly surprising, because the desired property to be modeled and to be predicted using the model is a sensory property that is sensorily evaluated by human expert panelists.

The predictive model is then used (a) to predict the softness performance, as estimated by softness performance index S, of other polyalkyleneoxy polysiloxane polymers when their quantitative structural properties are known (or by experimentally determining their quantitative structural properties by the procedures described herein below), and (b) to design new, currently non-existing polyalkyleneoxy polysiloxane polymers which potentially can provide superior softness performance. In an other aspect, the predictive model herein can be used to evaluate and explain what structural features of this class of polymers are the key driving force to provide the desired property (i.e., softness). Methods for Structural Characterization and Generation of Structural Descriptors for Polyalkyleneoxy Polysiloxane Polymers The polyalkyleneoxy polysiloxane polymer samples that are used to develop the predictive model performance in the present invention are technical grade, commercially available materials. These materials are optimally prepared by the suppliers to produce a high content of the intended materials, but also contain some amount of by-products, such as a low level of polyalkyleneoxy materials, and still contain a low level of some unreacted moieties, such as groups comprising unreacted allyl functional group. The analytical methods below take into account all these materials and groups.

$^{29}$Si-NMR and $^{13}$C-NMR methods, and hydroiodic acid sample hydrolysis followed by the quantitative GC analysis of the resulting alkyliodides are used to structurally characterize polyalkyleneoxy polysiloxanes of the graft type and the ABA type.

The $^{29}$Si-NMR spectra are obtained at 59.70 MHz using a Fourier transform spectrometer. Chromium (1,3-pentanedione)$_3$ is added to speed up the relaxation and suppress the nuclear Overhauser effect, caused by proton decoupling, on the silicon spectra. The $^{29}$Si-NMR spectra can differentiate and help to quantitatively yield the average number of Si atoms of different siloxane units, viz., the trimethylsiloxane $(CH_3)_3SiO$ units (designated as t#triSi), the dimethylsiloxane $Si(CH_3)_2O$ units (designated as t#diSi), and/or the methyl(alkylene)siloxane $Si(CH_3)(C_nH_{2n})O$ units (designated as #branch) that link with the poly(alkyleneoxy) groups wherein n is typically 3.

The $^{13}$C-NMR spectra are obtained at 75.57 MHz using a Fourier transform spectrometer. The chromium (1,3-pentanedione)$_3$ added to aid acquiring the silicon spectra, does not cause excessive broadening of the $^{13}$C spectra. The $^{13}$C-NMR spectra provide structural information of all of the carbon groups and can be used to determine the average number of pendant groups, the type of pendant groups, the capping groups, and the average number of unreacted allyl groups, if present.

Polyalkyleneoxy polysiloxanes are hydrolyzed by hydroiodic acid, a reaction catalyzed by adipic acid, to produce iodoethane, 1-iodopropane and 2-iodopropane. The hydrolyzed samples (hydrolysates) comprising iodoethane, 1-iodopropane and 2-iodopropane, are analyzed by gas chromatography with the FID detection against an internal standard (octane) and an external standard calibration with iodoalkanes to obtain the mass ratio of all ethyleneoxy units (designated as $w_{EO}$) and the mass ratio of all propyleneoxy units (designated as $w_{PO}$) in the polyalkyleneoxy polysiloxane molecules. Sum of mass ratio of all siloxane units (designated as $w_{Si}$), ethyleneoxy units and propyleneoxy units is equal to 1:

$$w_{Si}+w_{EO}+w_{PO}=1$$

The partial molecular weight of all siloxane units is determined from the average number of individual siloxane units determined from $^{29}$Si— and $^{13}$C-NMR and the respective molecular weight of the individual units according to the equation:

$$MW \text{ of all siloxane units}=2*89+(t\#diSi)*74+(\#branch)*101$$

wherein 74 is the molecular weight of each dimethylsiloxane unit, 89 is the molecular weight of each trimethylsiloxane unit, and 101 is the molecular weight of each linking siloxane $SiMe(CH_2CH_2CH_2)O$ unit. When the linking groups are different from $CH_2CH_2CH_2$, or when the molecule has only one or no $SiMe_3O$ units, the calculation can be modified accordingly.

Molecular weight of each polyalkyleneoxy polysiloxane molecule, designated as MW, is estimated from the mass ratio of all siloxane units, $w_{Si}$, (with $w_{Si}=1-w_{EO}-w_{PO}$) and the corresponding partial molecular weight of all siloxane units by the following equation:

$$MW=MW \text{ of all siloxane units}/w_{Si}$$

The average total number of ethyleneoxy units, —$CH_2CH_2O$—, designated as t#EO, and the average total number of propyleneoxy units, —$CH(CH_3)CH_2O$—, designated as t#PO, are derived from the molecular weight MW of the polyalkyleneoxy polysiloxane, the mass ratio $w_{EO}$ of the ethyleneoxy units and the mass ratio $w_{PO}$ of the propyleneoxy units, respectively, by the following equations:

$$t\#EO=MW*w_{EO}/44$$

and $$t\#PO=MW*w_{PO}/58$$

wherein 44 is the molecular weight of one ethyleneoxy unit —$CH_2CH_2O$—, and 58 is the molecular weight of one propyleneoxy unit —$CH(CH_3)CH_2O$—.

Weight % of all EO units (%EO), weight % of all PO units (%PO), and weight % of all siloxane units (%Si), are obtained by the following equations:

$$\%EO = 100 w_{EO} = 100 * t\#EO * 44/MW$$

$$\%PO = 100 w_{PO} = 100 * t\#EO * 58/MW,$$

and $$\%Si = 100 w_{Si} = 100 - \%EO - \%PO$$

The average number of ethyleneoxy units and the average number of propyleneoxy units, respectively, per polyalkyleneoxy pendant group (i.e., branch) (designated as #EO/branch and #PO/branch, respectively) are calculated by dividing the average total number of these units by the sum of the average number of methyl(alkylene)siloxane $Si(CH_3)(C_nH_{2n})O$ units (i.e., #branch) and the average number of unreacted allyl groups (i.e., #allyl) according to the following equation:

$$\#EO/branch = t\#EO/(\#branch + \#allyl),$$

and $$\#PO/branch = t\#PO/(\#branch + \#allyl)$$

The weight % of silicon atoms, designated as %Si atom, is calculated by the ratio of the total number of all siloxane groups multiplied by the molecular weight of silicon and divided by the MW:

$$\%Si\ atom = 100 * (total\ \#\ of\ all\ siloxane\ groups) * 28/MW$$

wherein $$total\ \#\ of\ all\ siloxane\ groups = t\#triSi + t\#diSi + \#branch$$

Nonlimiting examples of polyalkyleneoxy polysiloxane polymers that provide good fabric softness performance (with high S values) and are used in the development of the predictive model example herein are the following Silwet® surfactants available from OSi Specialties, Inc., Danbury, Conn.; and DC silicone copolyols available from Dow Corning Corporation, Midland, Mich.:

| Name | t#diSi[a] | t#EO[b] | % Si[c] | Experimentally Derived Softness Values | S Value[d] |
|---|---|---|---|---|---|
| DC-2 5573 | 194 | 754 | 19 | 26 | 30 |
| DC-190 | 116 | 411 | 20 | 26 | 26 |
| Silwet L-7230 | 68 | 151 | 24 | 19 | 24 |
| Silwet L-7001 | 82 | 254 | 20 | 28 | 24 |
| Silwet L-7622 | 90 | 107 | 62 | 27 | 24 |
| Silwet L-7087 | 75 | 263 | 18 | 24 | 23 |
| DC Q2 5220 | 137 | 854 | 15 | 22 | 22 |
| Silwet L-7220 | 40 | 91 | 17 | 19 | 22 |
| Silwet L-7002 | 25 | 127 | 17 | 22 | 16 |
| Silwet L-7602 | 24 | 42 | 56 | 19 | 14 |

[a] Approximated total average number of the $Si(CH_3)_2O$ units in the molecule.
[b] Approximated total average number of the ethyleneoxy $CH_2CH_2O$ units in the molecule.
[c] Approximated percent siloxane in the molecule.
[d] Softness Index as derived from mathematical function I.

The following polyalkyleneoxy polysiloxane polymers represent silicones that have poor softness performance (with S value of less than about 10), and are used in the development of the predictive model example herein.

| Name | t#diSi | t#EO | % Si | Experimentally Derived Softness Values | S Value |
|---|---|---|---|---|---|
| DC 2 5237 | 11 | 233 | 10 | 9 | 9 |
| Silwet L-7600 | 6.5 | 70 | 32 | 4 | 8 |
| Silwet L-7280 | 0 | 9 | 29 | 8 | 5 |
| Silwet L-77 | 0 | 10 | 37 | 5 | 3 |
| Silwet L-7607 | 0 | 17 | 32 | 3 | 3 |
| Silwet L-7608 | 0 | 8 | 44 | 3 | 3 |

The present invention also relates to a method of using the mathematical function I to (a) estimate and/or predict the fabric softening performance of a polyalkyleneoxy polysiloxane polymer, (b) select or identify the preferred polyalkyleneoxy polysiloxane polymers, and/or (c) design preferred polyalkyleneoxy polysiloxane polymers that provide superior fabric softening performance in a fabric softening spray composition and/or article of manufacture that comprises such fabric care composition.

Procedure to Estimate and/or Predict Fabric Softening Performance of a polyalkyleneoxy polysiloxane polymer: This is done by first determining the structural parameters required by mathematical function I, and then calculating the softness index S value using function I:

(a) Determine the approximated average total number of the $SiMe_2O$ units in the molecule (t#diSi), the number of methyl(alkylene)siloxane $Si(CH_3)(C_nH_{2n})O$ units, and total average number of siloxane units t#Si by $^{29}$Si-NMR and $^{13}$C-NMR methods as described hereinabove.

(b) Determine the approximated weight ratio of ethyleneoxy units $w_{EO}$, propyleneoxy units $w_{PO}$, and silicone units $w_{Si}$, per one polymer molecule, by the GC method as described hereinabove.

$$w_{Si} = 1 - w_{EO} - w_{PO}$$

(c) Determine the approximated average molecular weight (MW) of the polyalkyleneoxy polysiloxane by a combination of $^{29}$Si-NMR method and GC analysis of the hydrolysate of the polyalkyleneoxy polysiloxane as described hereinabove.

(d) Determine the approximated average total number of ethyleneoxy EO units (t#EO), and the approximated average total number of propyleneoxy PO units (t#PO) by the GC method as described hereinabove. The approximated weight percent total EO (%EO) and the weight percent total PO (%PO) are derived from t#EO and t#PO by the equations:

$$\%EO = 100 * w_{EO} = 100 \times (t\#EO \times 44)/MW$$

$$\%PO = 100 * w_{PO} = 100 \times (t\#PO \times 58)/MW$$

(e) Determine the approximated weight percent of all siloxane units (%Si) from the mass balance equation $$\%Si = 100 * w_{Si} = 100 - \%EO - \%PO (f)$$

Calculate the estimated/predicted softness index S value from mathematical function I by using the above values for t#diSi, t#EO, and %Si.

Procedure to Design Preferred Novel Polyalkyleneoxy Polysiloxane Polymers:

Predictive function I provides a method guiding the design of novel polyalkyleneoxy polysiloxane polymers that can provide superior fabric softening performance in the fabric softening compositions of the present invention. The method allows some flexible choices in designing new molecules, including, but not limited to, (i) choice of preferred type of molecules, e.g., polyethyleneoxy polysiloxane or polyethyleneoxy/polypropyleneoxy polysiloxane; (ii) choice of preferred molecular weight range; and/or (iii) choice of degree of hydrophicity/water compatibility by setting the preferred weight % of all ethyleneoxy EO units and the weight % of all siloxane units. A typical procedure includes the following steps to design a polyalkyleneoxy polysiloxane polymer wherein the polyalkyleneoxy groups are linked to the silicone backbone by the $CH_2CH_2CH_2$ linking groups, with no unreacted allyl groups, and the molecule has two terminal $SiMe_3O$ siloxane units:

(a) Set a desired S value, typically at least about 15, preferably at least about 20, more preferably at least about 25, and even more preferably at least about 30.

(b) Set a desired average molecular weight, MW, typically at least from about 1,200, preferably from about 2,000 to about 200,000, more preferably from about 4,000 to about 150,000, even more preferably from about 5,000 to about 120,000, and yet more preferably from about 6,000 to about 100,000.

(c) Set a desired weight % of all ethyleneoxy EO units (%EO) for the molecule, typically less than about 80, preferably from about 10 to about 75, more preferably from about 15 to about 70, and even more preferably from about 25 to about 50. The average total number of the ethyleneoxy units in the molecule (t#EO) is then derived from the equation $$\%EO = 100 \times (t\#EO \times 44)/MW$$

wherein t#EO is typically from about 25 to about 2,000, preferably from about 40 to about 1,500, more preferably from about 60 to about 1,200, and even more preferably from about 100 to about 1,000.

(d) Choose the type of polyalkyleneoxy polysiloxane, viz., polyethyleneoxy polysiloxane or polyethyleneoxy/polypropyleneoxy polysiloxane, then set the desired %Si, that is the weight percent of all siloxane units (which include the terminal trimethylsiloxane $Me_3SiO$ units, the dimethylsiloxane $SiMe_2O$ units, and/or the linking siloxane SiMe ($CH_2CH_2CH_2$)O units that link to the polyalkyleneoxy groups). For polyethyleneoxy polysiloxane %EO+%Si=100, while for polyethyleneoxy/polypropyleneoxy polysiloxane %EO+%PO+%Si=100.

(e) Use the desired values for S, t#EO and %Si to calculate t#diSi (the approximated average total number of dimethylsiloxane $SiMe_2O$ units in the molecule), using mathematical function I, wherein t#diSi is typically from about 4 to about 450, preferably at least about 15 to about 350, more preferably from about 30 to about 250, even more preferably from about 60 to about 250; (f) Calculate the average total number of all siloxane groups according to the following equation $$t\#Si = 1.119 \times t\#diSi + 3.788$$

(g) The average number of the polyalkyleneoxy pendant groups (branches) are $$\#branch = t\#Si - t\#diSi - 2$$

for branched graft copolymers.

When the molecule has only one or no $SiMe_3O$ units, the calculation can be modified accordingly.

The descriptors in the model are very global in nature. This means that the descriptors characterize general features of all of the molecules in this class, and not just focusing on very compound-specific features (i.e., descriptors that are needed to characterize only a small fraction of the training set compounds). Since 90% of the variance in the experimental measurements is explained by the model, as measured by $R^2$, the risk of error from small excursions beyond the scope of the training set (i.e., setting an S value of, e.g., 35) is diminished.

Examples of the highly performing polyethyleneoxy polysiloxane polymers which are derived from mathematical function I and useful in the fabric softening spray compositions includes:

| Ex. No. | MW | % EO | % PO | % Si | t#diSi | No. of Branches[a] | t#EO | t#PO | Predicted S |
|---|---|---|---|---|---|---|---|---|---|
| 1 | 37,400 | 43 | 6 | 51 | 217 | 28 | 366 | 39 | 35 |
| 2 | 32,100 | 42 | 0 | 58 | 212 | 27 | 306 | 0 | 35 |
| 3 | 40,000 | 42 | 12 | 46 | 212 | 27 | 382 | 83 | 34 |
| 4 | 57,200 | 39 | 27 | 34 | 219 | 28 | 507 | 266 | 34 |
| 5 | 47,400 | 36 | 26 | 38 | 205 | 26 | 388 | 212 | 35 |
| 6 | 33,300 | 34 | 16 | 50 | 190 | 24 | 257 | 92 | 35 |
| 7 | 78,300 | 30 | 46 | 24 | 212 | 27 | 534 | 621 | 35 |
| 8 | 36,200 | 30 | 26 | 44 | 181 | 23 | 247 | 162 | 35 |
| 9 | 27,300 | 28 | 14 | 58 | 180 | 23 | 174 | 66 | 35 |
| 10 | 32,700 | 26 | 29 | 45 | 168 | 22 | 193 | 164 | 35 |
| 11 | 89,800 | 22 | 59 | 19 | 190 | 24 | 449 | 913 | 35 |
| 12 | 63,500 | 10 | 73 | 17 | 121 | 16 | 144 | 799 | 35 |
| 13 | 48,300 | 10 | 69 | 21 | 116 | 16 | 110 | 575 | 35 |
| 14 | 16900 | 16 | 0 | 84 | 161 | 21 | 61 | 0 | 35 |
| 15 | 31500 | 43 | 0 | 57 | 205 | 26 | 306 | 0 | 34 |
| 16 | 21100 | 26 | 0 | 74 | 177 | 23 | 127 | 0 | 35 |
| 17 | 43,000 | 51 | 4 | 45 | 220 | 28 | 498 | 30 | 33 |
| 18 | 58,900 | 46 | 21 | 33 | 220 | 28 | 616 | 213 | 33 |
| 19 | 51,500 | 40 | 26 | 34 | 202 | 26 | 468 | 231 | 33 |
| 20 | 41,700 | 33 | 32 | 35 | 168 | 22 | 313 | 230 | 33 |
| 21 | 62,500 | 33 | 41 | 26 | 184 | 24 | 469 | 442 | 33 |
| 22 | 23,100 | 31 | 6 | 63 | 166 | 22 | 163 | 24 | 33 |

-continued

| Ex. No. | MW | % EO | % PO | % Si | t#diSi | No. of Branches[a] | t#EO | t#PO | Predicted S |
|---|---|---|---|---|---|---|---|---|---|
| 23 | 32,300 | 25 | 34 | 41 | 151 | 20 | 184 | 189 | 33 |
| 24 | 22,900 | 23 | 19 | 58 | 150 | 20 | 120 | 75 | 33 |
| 25 | 23,900 | 22 | 23 | 55 | 147 | 19 | 120 | 95 | 33 |
| 26 | 87,600 | 21 | 63 | 16 | 158 | 21 | 418 | 952 | 32 |
| 27 | 69,900 | 19 | 63 | 18 | 141 | 19 | 302 | 759 | 33 |
| 28 | 33300 | 47 | 0 | 53 | 203 | 26 | 352 | 0 | 33 |
| 29 | 19900 | 28 | 0 | 72 | 162 | 21 | 128 | 0 | 33 |
| 30 | 26300 | 39 | 0 | 61 | 182 | 23 | 234 | 0 | 33 |
| 31 | 49,100 | 59 | 4 | 37 | 206 | 26 | 658 | 34 | 30 |
| 32 | 50,000 | 54 | 11 | 35 | 197 | 25 | 614 | 95 | 30 |
| 33 | 66,400 | 54 | 17 | 29 | 219 | 28 | 815 | 195 | 30 |
| 34 | 30,400 | 48 | 4 | 48 | 165 | 21 | 332 | 21 | 30 |
| 35 | 26,300 | 42 | 5 | 53 | 166 | 21 | 251 | 23 | 31 |
| 36 | 21,400 | 40 | 0 | 60 | 146 | 19 | 195 | 0 | 30 |
| 37 | 32,200 | 40 | 19 | 41 | 150 | 20 | 293 | 105 | 30 |
| 38 | 25,000 | 32 | 23 | 45 | 128 | 17 | 182 | 99 | 30 |
| 39 | 22,700 | 31 | 19 | 50 | 127 | 17 | 160 | 74 | 30 |
| 40 | 34,100 | 28 | 38 | 34 | 132 | 17 | 217 | 223 | 31 |
| 41 | 19,600 | 19 | 34 | 47 | 104 | 14 | 85 | 115 | 30 |
| 42 | 16,100 | 15 | 29 | 56 | 101 | 14 | 55 | 81 | 30 |
| 43 | 41,000 | 12 | 70 | 18 | 82 | 11 | 112 | 495 | 29 |
| 44 | 15300 | 23 | 0 | 77 | 132 | 17 | 81 | 0 | 30 |
| 45 | 26200 | 44 | 0 | 56 | 170 | 22 | 261 | 0 | 31 |
| 46 | 43700 | 58 | 0 | 42 | 208 | 27 | 577 | 0 | 31 |
| 47 | 33,400 | 63 | 0 | 37 | 140 | 18 | 478 | 0 | 25 |
| 48 | 55,900 | 63 | 11 | 26 | 168 | 22 | 800 | 106 | 25 |
| 49 | 39,200 | 62 | 6 | 32 | 144 | 19 | 552 | 41 | 25 |
| 50 | 50,400 | 60 | 12 | 28 | 160 | 21 | 687 | 104 | 25 |
| 51 | 29,100 | 49 | 15 | 36 | 118 | 16 | 324 | 75 | 25 |
| 52 | 23,400 | 46 | 14 | 40 | 104 | 14 | 245 | 56 | 25 |
| 53 | 16,400 | 36 | 16 | 48 | 88 | 12 | 134 | 45 | 25 |
| 54 | 12,900 | 34 | 0 | 66 | 94 | 13 | 100 | 0 | 25 |
| 55 | 22,000 | 32 | 35 | 33 | 81 | 11 | 160 | 133 | 25 |
| 56 | 25,800 | 20 | 57 | 23 | 64 | 9 | 117 | 254 | 25 |
| 57 | 17,800 | 19 | 49 | 32 | 62 | 9 | 77 | 150 | 25 |
| 58 | 15,300 | 16 | 48 | 36 | 60 | 9 | 56 | 127 | 25 |
| 59 | 8700 | 15 | 0 | 85 | 82 | 12 | 29 | 0 | 25 |
| 60 | 12300 | 33 | 0 | 67 | 91 | 13 | 93 | 0 | 25 |
| 61 | 20400 | 52 | 0 | 48 | 110 | 15 | 239 | 0 | 25 |

[a]The average number of branches is #branch, i.e., the average number of polyalkyleneoxy pendant groups in the molecule.

The preparation of polyalkyleneoxy polysiloxane polymers is well known in the art. The polyalkyleneoxy polysiloxanes examplified hereinabove can be prepared according to the procedure set forth in U.S. Pat. No. 3,299,112, incorporated herein by reference. Typically, polyalkyleneoxy polysiloxanes are readily prepared by an addition reaction between a hydrosiloxane (i.e., a siloxane containing silicon-bonded hydrogen) and an alkenyl ether (e.g., a vinyl, allyl, or methallyl ether) of an alkoxy or hydroxy end-blocked polyalkyleneoxy). The reaction conditions employed in addition reactions of this type are well known in the art and in general involve heating the reactants (e.g., at a temperature of from about 85° C. to 110° C.) in the presence of a platinum catalyst (e.g., chloroplatinic acid) and a solvent (e.g., toluene). Additional disclosures of preparation methods for polyalkyleneoxy polysiloxanes can be found in *Silicone Surfactants*, R. M. Hill. (Ed.), Marcel Dekker, Inc. (1999), Chapter 2, said publication being incorporated herein by reference.

The method of the present invention can also be used to develop predictive functions for desired properties of other silicone polymers, including, but not limited to, linear, branched and cyclic polydimethylsiloxanes, and derivatives thereof, silicone random copolymers, silicone-organic (block) copolymers, and mixtures thereof. Nonlimiting examples of applicable silicone polymers are as follows:

Polyalkyl and/or phenylsilicones with the general structure:

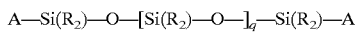

wherein each R group can be alkyl, aryl, hydroxy, or hydroxyalkyl group, and mixtures thereof, each A group which blocks the ends of the silicone chain can be hydrogen, methyl, methoxy, ethoxy, hydroxy, propoxy, and aryloxy group. The most common silicones of this class are polydimethylsiloxanes wherein R and A group are methyl. Silicones herein also comprise those having, e.g., silane Si—H bonds and/or silanol Si—OH bonds.

Cyclic silicone of the formula $[(CH_3)_2SiO]_n$ wherein n ranges between about 3 to about 7.

Cationic and/or aminofunctional silicones corresponding to the general formula:

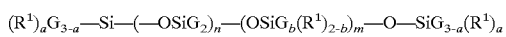

wherein each G can be hydrogen, phenyl, OH, and/or $C_1$–$C_8$ alkyl; a is 0 or an integer from 1 to 3; b is 0 or 1; $R^1$ is a monovalent radical of formula $C_pH_{2p}L$ in which p is an integer from 2 to 8 and L is selected from the group consisting of:

—N($R^2$)CH$_2$—CH$_2$—N($R^2$)$_2$;

—N($R^2$)$_2$;

—N$^+$($R^2$)$_3$A$^-$;

and

—N$^+$($R^2$)CH$_2$—CH$_2$N$^+$H$_2$A$^-$ wherein n and m are integers; each $R^2$ is chosen from the group consisting of hydrogen, phenyl, benzyl, saturated hydrocarbon radical, and each A$^-$ denotes compatible anion, e.g., a halide ion.

Examples of cationic and/or aminofunctional silicones include amodimethicones, with the formula:

HO—[Si(CH$_3$)$_2$—O]$_m$—{Si(OH)[(CH$_2$)$_3$—NH—(CH$_2$)$_2$—NH$_2$]O}$_{n-H}$ wherein m and n are integers;

(CH$_3$)$_3$Si—[O—Si(CH$_3$)$_2$]$_n$—{OSi(CH$_3$)[(CH$_2$)$_3$—NH—(CH$_2$)$_2$—NH$_2$]}$_m$—OSi(CH$_3$)$_3$ wherein n and m are integers; and $R^3$—N$^+$(CH$_3$)$_2$—Z—[Si(CH$_3$)$_2$O]$_f$—Si(CH$_3$)$_2$—Z—N$^+$(CH$_3$)$_2$—$R^3$·2CH$_3$COO$^-$ wherein Z is —CH$_2$—CH(OH)—CH$_2$O—CH$_2$)$_3$—; $R^3$ denotes a long chain alkyl group; and f denotes an integer of at least about 2.

Silicone graft copolymers, such as silicone graft copolymers comprising acrylate groups, along with methods of making them, are described in U.S. Pat. No. 5,658,557, Bolich et al., issued Aug. 19, 1997, U.S. Pat. No. 4,693,935, Mazurek, issued Sep. 15, 1987, and U.S. Pat. No. 4,728,571, Clemens et al., issued Mar. 1, 1988. Additional silicone-containing polymers are disclosed in U.S. Pat. Nos. 5,480,634, Hayama et al, issued Oct. 2, 1996, U.S. Pat. No. 5,166,276, Hayama et al., issued Nov. 24, 1992, U.S. Pat. No. 5,061,481, issued Oct. 29, 1991, Suzuki et al., U.S. Pat. No. 5,106,609, Bolich et al., issued Apr. 21, 1992, U.S. Pat. No. 5,100,658, Bolich et al., issued Mar. 31, 1992, U.S. Pat. No. 5,100,657, Ansher-Jackson, et al., issued Mar. 31, 1992, U.S. Pat. No. 5,104,646, Bolich et al., issued Apr. 14, 1992, all of which are incorporated herein by reference. These polymers include copolymers having a vinyl polymeric backbone and having monovalent siloxane polymeric moieties grafted to said backbone, and components consisting of non-silicone hydrophilic and hydrophobic monomers. The silicone-containing monomers are exemplified by the general formula:

X(Y)$_n$Si(R)$_{3-m}$Z$_m$ wherein X is a polymerizable group, such as a vinyl group, which is part of the backbone of the polymer; Y is a divalent linking group; R is a hydrogen, hydroxyl, lower alkyl (e.g. $C_1$–$C_4$), aryl, alkaryl, alkoxy, or alkylamino; Z is a monovalent polymeric siloxane moiety having an average molecular weight of at least about 500, is essentially unreactive under copolymerization conditions, and is pendant from the vinyl polymeric backbone described above; n is 0 or 1; and m is an integer from 1 to 3. Nonlimiting examples of silicone-containing monomers have the following formulas:

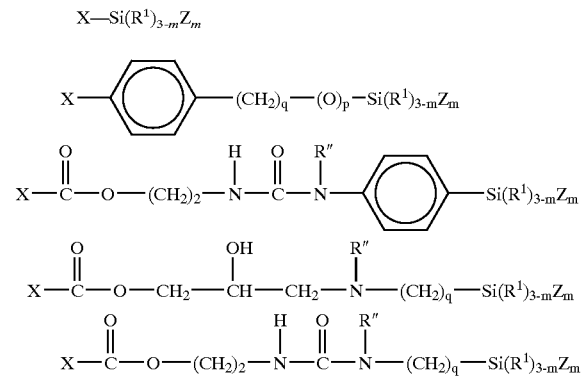

wherein m is an integer from 1 to 3; p is 0 or 1; q is an integer from 2 to 6; n is an integer from 0 to 4; $R^1$ is hydrogen, lower alkyl, alkoxy, hydroxyl, aryl, alkylamino; R" is alkyl or hydrogen; X is CH($R^3$)==C($R^4$)—; $R^3$ is hydrogen or —COOH; $R^4$ is hydrogen, methyl or —CH$_2$COOH; Z is $R^5$—[Si($R^6$)($R^7$)—O—]$_r$, wherein $R^5$, $R^6$, and $R^7$, independently are lower alkyl, alkoxy, alkylamino, hydrogen or hydroxyl, preferably alkyl; and r is an integer of from about 10 to about 700.

Silicone block copolymers comprise repeating block units of polysiloxanes. Examples of silicone-containing block copolymers are found in U.S. Pat. No. 5,523,365, to Geck et al., issued Jun. 4, 1996; U.S. Pat. No. 4,689,289, to Crivello, issued Aug. 25, 1987; U.S. Pat. No. 4,584,356, to Crivello, issued Apr. 22, 1986; *Macromolecular Design, Concept & Practice*, Ed: M. K. Mishra, Polymer Frontiers International, Inc., Hopewell Jct., NY (1994), and *Block Copolymers*, A. Noshay and J. E. McGrath, Academic Press, NY (1977), which are all incorporated herein by reference. Other silicone block copolymers are those described, along with methods of making them, in the above referenced and incorporated U.S. Pat. No. 5,658,577.

The silicone-containing block copolymers can be described by the formulas A-B, A-B-A, and -(A-B)$_n$- wherein n is an integer of 2 or greater. A-B represents a diblock structure, A-B-A represents a triblock structure, and -(A-B)$_n$- represents a multiblock structure. The block copolymers can comprise mixtures of diblocks, triblocks, and higher multiblock combinations as well as small amounts of homopolymers.

The silicone block portion, B, can be represented by the following polymeric structure —(SiR$_2$O)$_m$—, wherein each R is independently selected from the group consisting of hydrogen, hydroxyl, $C_1$–$C_6$ alkyl, $C_1$–$C_6$ alkoxy, $C_2$–$C_6$ alkylamino, styryl, phenyl, $C_1$–$C_6$ alkyl or alkoxy-substituted phenyl; and m is an integer of about 10 or greater.

The non-silicone block, A, comprises monomers selected from the monomers as described hereinabove in reference to the non-silicone hydrophilic and hydrophobic monomers for the silicone grafted copolymers.

Sulfur-linked silicone-containing copolymers including block copolymers. As used herein in reference to silicone containing copolymers, the term "sulfur-linked" means that the copolymer contains a sulfur linkage (i.e., —S—), a disulfide linkage (i.e., —S—S—), or a sulfhydryl group (i.e., —SH). These sulfur-linked silicone-containing copolymers are represented by the following general formula:

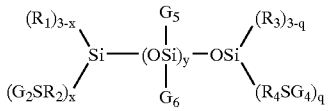

wherein each $G_5$ and $G_6$ is independently selected from the group consisting of alkyl, aryl, alkaryl, alkoxy, alkylamino, fluoroalkyl, hydrogen, and —ZSA, wherein A represents a vinyl polymeric segment consisting essentially of polymerized free radically polymerizable monomer, and Z is a divalent linking group (Useful divalent linking groups Z include but are not limited to the following: $C_1$ to $C_{10}$ alkylene, alkarylene, arylene, and alkoxyalkylene);

each $G_2$ comprises A;

each $G_4$ comprises A;

each $R_1$ is a monovalent moiety selected from the group consisting of alkyl, aryl, alkaryl, alkoxy, alkylamino, fluoroalkyl, hydrogen, and hydroxyl;

each $R_2$ is a divalent linking group (suitable divalent linking groups include but are not limited to the following: $C_1$ to $C_{10}$ alkylene, arylene, alkarylene, and alkoxyalkylene);

each $R_3$ represents monovalent moieties which can independently be the same or different and are selected from the group consisting of alkyl, aryl, alkaryl, alkoxy, alkylamino, fluoroalkyl, hydrogen, and hydroxyl;

each $R_4$ is a divalent linking group (suitable divalent linking groups include but are not limited to the following: $C_1$ to $C_{10}$ alkylene, arylene, alkarylene, and alkoxyalkylene);

x is an integer of 0–3;

y is an integer of 5 or greater; and q is an integer of 0–3;

wherein at least one of the following is true:

q is an integer of at least 1;

x is an integer of at least 1;

$G_5$ comprises at least one —ZSA moiety; or $G_6$ comprises at least one —ZSA moiety.

Sulfur linked silicone copolymers are described in more detail in U.S. Pat. No. 5,468,477, to Kumar et al., issued Nov. 21, 1995, and PCT Application No. WO 95/03776, assigned to 3M, published Feb. 9, 1995, which are incorporated herein by reference.

Structural descriptors for the silicones and derivatives hereinabove can be generated and/or derived exprimentally by using analytical methods used for the analyses of the polyalkyleneoxy polysiloxane polymers and other analytical methods. The appropriate structural descriptors can then be used develop predictive functions for desired properties of these silicone polymers according to the method of the present invention. All of the patents, patent applications, and references referred to herein are incorporated, either wholly, or in relevant part, by reference. All parts, ratios, and percentages herein are by weight and all numerical limits are used with the normal degree of accuracy afforded by the art unless otherwise specified.

What is claimed is:

1. A method for identifying a predictive model from which to select existing polymers, and/or to prepare new polymers having a desired property, the method comprising the steps of:
    a. identifying a set of existing polymers;
    b. determining the desired property for each of the polymers in the set, wherein the property of each polymer has a numerical value;
    c. generating quantitative structural descriptors that characterize at least a portion of the molecular structure of each polymer of the set of polymers; and
    d. identifying a mathematical function that relates a selected group of descriptors to the desired property, said group comprises at least 2 quantitative structural descriptors, the predictive model comprising the identified mathematical function;

wherein the desired property can be provided by the neat, undiluted polymer or by a composition comprising the polymer.

2. The method of claim 1, wherein the quantitative structural descriptors characterize the whole molecular structure of each polymer.

3. The method of claim 1, wherein said descriptors are distinct descriptors.

4. The method of claim 1, wherein the number of descriptors of step d is from about 2 to about 10.

5. The method of claim 4, wherein the number of descriptors is from about 2 to about 6.

6. The method of claim 5, wherein the number of descriptors is from about 2 to about 4.

7. The method of claim 1, wherein there are at least about 10 unique polymer samples in the set of polymers.

8. The method of claim 7, wherein the set of existing polymers comprises at least about 15 unique polymer samples.

9. The method of claim 8, wherein the set comprises at least about 20 unique polymer samples.

10. The method of claim 1, wherein the quantitative structural descriptors are experimentally derived using one or more analytical methods.

11. The method of claim 10, wherein the descriptors are selected from the group consisting of molecular weight, molecular weight distribution, structure type, weight and/or molar percentage(s) of one or all atomic elements, average weight and/or molar percentage of each molecular group, number of each molecular group, number of each monomer, degree of unsaturation, degree of branching within a molecule and/or part of a molecule, weight percentage of each atomic elements in a branching group, number of each molecular groups in a branching group, number of each types and/or number of functional groups and/or their percentage, types and/or number and/or percentage of repeating units, monomer units or other subunits, the spread of the distribution of a value above, functional transforms thereof, and mixtures thereof.

12. The method of claim 1, wherein the descriptors of step d additionally comprise one or more descriptors selected from the group consisting of computed structural descriptors for the whole molecule, monomers and/or subunits; bulk physical property descriptors; compositional descriptors; and mixtures thereof.

13. The method of claim 12, wherein said computed structural descriptor is selected from the group consisting of length, width, depth, cross section area, volume, and surface area, topological indices for the monomer units or other subunits, electronic descriptors for the monomer units or other subunits selected from the group consisting of electric and magnetic moments, polarizabilities, orbital energies and/or excitation energies, solubility descriptors selected from the group consisting of octanol/water partition coefficient and/or aqueous solubility, and CPSA descriptors.

14. The method of claim 12, wherein said bulk physical property descriptor is selected from the group consisting of viscosity, glass transition temperature, melting point, density, solubility, cloud point, heat capacity, interfacial tension, interfacial adhesion, refractive index, stress relaxation, sheer, conductivity, permeability, diamagnetic susceptibility, thermal conductivity, and mixtures thereof.

15. The method of claim 12, wherein said compositional descriptor is selected from the group consisting of weight percent of one or more starting ingredients, reaction temperature, reaction time, and reaction pressure.

16. The method of claim 1, wherein the mathematical function is identified using a multivariate statistical analysis methodology.

17. The method of claim 16, wherein the mathematical function can generate predicted values of the structural descriptors which can be correlated with the experimentally derived values with a correlation coefficient of at least about 0.6.

18. The method of claim 17, wherein the correlation coefficient is at least about 0.7.

19. The method of claim 18, wherein the correlation coefficient is at least about 0.8.

20. The method of claim 19, wherein the correlation coefficient is at least about 0.9.

21. The method of claim 16, wherein a computer is used to perform the multivariate statistical analysis.

22. The method of claim 1, further comprising the steps of
e. identifying one or more additional mathematical function(s); and
f. determining which mathematical function more accurately correlates molecular structure with the desired property.

23. The method of claim 1, further comprising the step of selecting existing polymers other than those in step a that have a molecular structure that satisfies the mathematical function identified in step d.

24. The method of claim 1, further comprising the step of preparing new polymers that have a molecular structure that satisfies the mathematical function identified in step d.

25. The method of claim 1, wherein the polymer has an average molecular weight of about 600 or higher.

26. The method of claim 25, wherein the polymer has an average molecular weight of about 1,000 or higher.

27. The method of claim 1, wherein the desired property can be determined instrumentally or by the senses.

28. The method of claim 1, wherein the desired property is a useful functional property provided by the polymer in a consumer product composition and/or industrial composition.

29. The method of claim 28, wherein the desired property is a consumer relevant property provided by the polymer under use conditions in a consumer product composition comprising the polymer.

30. The method of claim 29, wherein the composition is selected from the group consisting of fiber and fabric care composition, hair care composition, skin care composition, cosmetic composition, nail care composition, lip care composition, oral and/or dental care composition, pet care composition, hard surface care composition, soft surface care composition, home care composition, car care composition, food composition, beverage composition, disposable paper composition, baby care composition, human health care composition, and animal health care composition.

31. The method of claim 30, wherein the composition is a fiber and fabric care composition and the functional property that is desired is selected from the group consisting of fabric color restoration, color maintenance, fading resistance or reduction, fabric softening, fabric conditioning, wrinkle control, wrinkle resistance or reduction, shape retention, wear resistance or reduction, pilling prevention or reduction, soil release, static control, shrinkage reduction, long lasting freshness, odor control, allergen control, flame resistance, waterproofing, and mixtures thereof.

32. The method of claim 30, wherein the composition is a car care composition and the functional property that is desired is selected from the group consisting of long lasting shine/gloss, color deepening and/or maintenance, glide/lubricity, and mixtures thereof.

33. The method of claim 30, wherein the composition is a hair care composition and the functional property that is desired is selected from the group consisting of long lasting shine, ease of combing and mixtures thereof.

34. The method of claim 28, wherein the industrial composition is selected from the group consisting of textile treatment composition, coating composition, ink composition, wood treatment composition, adhesive composition, fluid drilling composition, wax composition, and plastic molding composition.

35. The method of claim 1, wherein the polymer is selected from the group consisting of polystryrenes, polyvinylcarboxylic acid, polysiloxanes and derivatives thereof; polyethyleneoxy/polypropyleneoxy block copolymers, derivatives thereof, homologues thereof, and mixtures thereof; polysaccharide polymers, homologues thereof, derivatives thereof, and mixtures thereof; polyvinyl homopolymers and/or copolymers, and derivatives thereof; polyamines and chemically modified derivatives thereof, and mixtures thereof; polyamide, homologues thereof and/or derivatives thereof, and mixtures thereof; polyterephthalates, isomers thereof, homologues thereof, and/or derivatives thereof, and mixtures thereof; polyesters and chemically modified derivatives thereof; polyurethane; condensation products of imidazole and epichlorhydrin, and mixtures thereof; aromatic polymeric condensates of formaldehyde, and mixtures thereof.

36. The method of claim 35, wherein said polymer can be further modified to provide desired properties by incorporation of one or more of aryl, alkyl, allyl, methyl, ethyl, ethoxylate, propoxylate, nitro, amino, imido, sulpho, carbo, phospho, groups, and mixtures thereof; wherein the polyvinyl homopolymers and/or copolymers are selected from the group consisting of polyvinyl acetate and partially hydrolyzed materials thereof; polyvinyl alcohol; block and/or random copolymers of polyvinyl pyridine N-oxide; polyvinyl pyrrolidone; polyvinyl imidazole; block and/or random copolymer of polyvinyl pyrrolidone and polyvinyl imidazole, and mixtures thereof; wherein the polystyrenes are selected from a group consisting of block and/or random copolymer of polystyrene with polymaleate, polyacrylate, or polymethacrylate; wherein said polyvinyl carboxylic acids are selected from polyacrylic acid and/or polymethacrylic acid, alkyl esters thereof, amides thereof, and mixtures thereof; and wherein said polyamide is selected from the group consisting of proteins, peptides, nylon, polyamideamines, and mixtures thereof.

37. The method of claim 35, wherein the polymer is polysiloxane and derivatives thereof.

38. The method of claim 37, wherein the polysiloxane is selected from the group consisting of linear, branched and/or cyclic polydimethylsiloxanes, and derivatives thereof, silicone random copolymers, silicone-organic (block) copolymers, and mixtures thereof.

39. The method of claim 38, wherein the polymer is polyalkyleneoxy polysiloxane.

40. The method of claim 39, wherein the quantitative structural descriptors are selected from the group consisting of molecular weight, t#triSi, t#diSi, #branch, #allyl, t#EO, t#PO, %Si, %EO, %PO, %Si, %Si atom, #EO/branch, #PO/branch, $w_{Si}$, $w_{EO}$, $w_{PO}$, functional transforms thereof, and mixtures thereof.

* * * * *